United States Patent
Asahi et al.

(10) Patent No.: US 7,597,278 B2
(45) Date of Patent: Oct. 6, 2009

(54) METHOD OF PRODUCING MEDICINAL NANOPARTICLE SUSPENSION

(75) Inventors: Tsuyoshi Asahi, Osaka (JP); Hiroshi Masuhara, Osaka (JP); Teruki Sugiyama, Osaka (JP); Isamu Oh, Osaka (JP); Sen-ichi Ryo, Osaka (JP); Hiroyuki Kato, Tokyo (JP); Isao Umeda, Tokyo (JP)

(73) Assignees: Osaka University, Osaka (JP); Absize, Inc., Osaka (JP); Ebara Corporation, Tokyo (JP)

( * ) Notice: Subject to any disclaimer, the term of this patent is extended or adjusted under 35 U.S.C. 154(b) by 109 days.

(21) Appl. No.: 11/798,621

(22) Filed: May 15, 2007

(65) Prior Publication Data

US 2008/0237376 A1    Oct. 2, 2008

(30) Foreign Application Priority Data

May 15, 2006    (JP)    ............................. 2006-135878

(51) Int. Cl.
*B02C 19/00*    (2006.01)
(52) U.S. Cl. ............................................. 241/1; 241/21
(58) Field of Classification Search .................... 241/1, 241/21, 301; 424/489
See application file for complete search history.

(56) References Cited

U.S. PATENT DOCUMENTS

| | | | |
|---|---|---|---|
| 5,145,684 | A | 9/1992 | Liversidge et al. |
| 5,510,118 | A | 4/1996 | Bosch et al. |
| 2006/0103060 | A1 | 5/2006 | Kawakami et al. |
| 2006/0251584 | A1 | 11/2006 | Nagare et al. |
| 2006/0257489 | A1 | 11/2006 | Kawakami et al. |
| 2007/0114306 | A1 | 5/2007 | Kawakami et al. |

FOREIGN PATENT DOCUMENTS

| | | |
|---|---|---|
| JP | 2001-113159 | 4/2001 |
| JP | 2004-167316 | 6/2004 |
| JP | 2005-125204 | 5/2005 |
| JP | 2005-125258 | 5/2005 |
| JP | 2005-238342 | 9/2005 |
| JP | 2005-334782 | 12/2005 |
| JP | 2006-026503 | 2/2006 |
| JP | 2007-045674 | 2/2007 |
| WO | WO 01/45677 | 6/2001 |
| WO | WO 2004080586 | * 9/2004 |
| WO | WO 2005/049213 | 6/2005 |
| WO | WO 2005/082521 | 9/2005 |
| WO | WO 2005/092489 | 10/2005 |

OTHER PUBLICATIONS

Hiroshi Masuhara, "Tailoring nanoparticles of aromatic and dye molecules by excimer laser irradiation", Applied Surface Science 168 (2000) 85-88.

Mitsuo Hiramatsu, "Enhancement of organic nanoparticle preparation by laser ablation in aqueous solution using surfactants", Applied Surface Science 210 (2003) 171-176.

S. Nagare, "Reagglomeration mechanism of drug nanoparticles by pulsed laser deposition", Solid State Ionics 172 (2004) 243-247.

Sanshiro Nagare, "Indomethacin nanoparticles directly deposited on the fluidized particulate excipient by pulsed laser deposition", Journal of Nanoparticle Research (2004).

* cited by examiner

*Primary Examiner*—Mark Rosenbaum
(74) *Attorney, Agent, or Firm*—Kubotera & Associates, LLC

(57) ABSTRACT

A method of producing a medicinal nanoparticle suspension is provided, wherein a medicinal ingredient added in a suspending solution is ground to form nanoparticles of the medicinal ingredient by irradiating the suspending solution with a laser. The process is implemented after adding a poorly water-soluble or water-insoluble medicinal ingredient of a drug in a poor solvent to form the suspending solution.

8 Claims, 1 Drawing Sheet

METHOD OF PRODUCING MEDICINAL NANOPARTICLE SUSPENSION

FIELD OF THE INVENTION

The present invention relates to a method of producing a medicinal nanoparticle suspension. The present invention particularly relates to a method of producing a medicinal nanoparticle suspension through making nanoparticles of a poorly water-soluble or water-insoluble medicinal ingredient of a drug without impurity contamination.

DESCRIPTION OF BACKGROUND ART

Recently, nanometer-size particles (nanoparticles) with an average diameter of less than 1 μm are applied to various technical fields. In the field of pharmaceuticals, it is expected that the nanometer-size particles provide advantageous effects.

As an example of the advantageous effects, a poorly water-soluble or water-insoluble medicinal ingredient is converted into nanoparticles. It is found that intravenous injection of the nanoparticles dispersed in water does not form thrombus. In addition, the injection may enhance medicinal ingredient absorption in vivo. Therefore, it is expected that the medicinal nanoparticles are utilized in a drug delivery system (DDS), in which a pharmaceutical agent or gene is delivered to an affected part, as an effective measure for cancer therapy or gene therapy.

Conventionally, few methods for preparing the medicinal nanoparticles of a drug have been known. The conventional methods include, for example, a wet grinding method (refer to Patent Reference 1), in which a wet mill is used to grind a medicinal ingredient in presence of a surfactant agent, so that the medicinal ingredient is converted into nanoparticles; a high pressure homogenization method (refer to Patent Reference 2), in which a high pressure is applied to homogenize a medicinal ingredient for producing nanoparticles of the medical ingredient; and a fluid bed spray-drying method (refer to Patent Reference 3), in which an organic solution of a poorly water-soluble or water-insoluble compound is sprayed to a fluidized bed of carrier excipient particles under a condition that an organic solvent is removed from the organic solution, thereby obtaining a mixture of the medicinal nanoparticles and the carrier excipient particles.

However, there are several problems in the conventional methods mentioned above.

In the first method, or the wet grinding method, metal impurities coming from a metal ball for the grinding process tend to mix in the medicinal ingredient. Therefore, it is difficult to obtain a suspension exclusively comprising the medicinal nanoparticles.

The second method, or the high pressure homogenization method, is used to minimize a size of liquid globules of emulsion and liposome, and its applicability to a solid substance depends on a physical property of the substance. Therefore, the method is applicable only to limited types of medicinal ingredients.

When the third method, or the fluid bed spray-drying method, is used, the organic solvent may remain in the obtained mixture. Therefore, it is difficult to obtain a suspension exclusively comprising the medicinal nanoparticles.

As described above, with the conventional methods, it is possible to convert the medicinal ingredient into the medicinal nanoparticles. However, in order to safely administrate the medicinal nanoparticles to a human body, several critical problems have to be solved.

[Patent Reference 1] U.S. Pat. No. 5,145,684
[Patent Reference 1] U.S. Pat. No. 5,510,118
[Patent Reference 1] Japanese Patent Publication No. 2003-518038

In order to overcome these problems in the prior art, the present invention provides a method of obtaining a medicinal nanoparticle suspension suitable for administration to a human body. The method of the present invention makes it possible to prepare nanopaticles of a poorly water-soluble or water-insoluble medicinal ingredient while preventing impurity from contaminating.

SUMMARY OF THE INVENTION

The present invention relates to a method of producing a medicinal nanoparticle suspension, wherein a medicinal ingredient in a suspending solution is ground to form nanoparticles of the medicinal ingredient by irradiating the suspending solution with a laser, after a poorly water-soluble or water-insoluble medicinal ingredient of a drug is added into a poor solvent to form the suspending solution.

The present invention relates to the method of producing the medicinal nanoparticle suspension, wherein ultrasonic waves are applied to the poor solvent with the medicinal ingredient mixed therein, before the laser is irradiated to the suspending solution.

The present invention relates to the method of producing the medicinal nanoparticle suspension, wherein the laser is irradiated while the poor solvent with the medicinal ingredient mixed therein is stirred.

The present invention relates to the method of producing the medicinal nanoparticle suspension, wherein the suspending solution is placed quietly or centrifuged after the laser is irradiated.

The present invention relates to the method of producing the medicinal nanoparticle suspension, wherein a pulse laser is used as the laser.

The present invention relates to the method of producing the medicinal nanoparticle suspension, wherein the pulse laser has a pulse width of several-ten femtoseconds to several-hundred nanoseconds.

The present invention relates to the method of producing the medicinal nanoparticle suspensions, wherein the pulse laser is irradiated at an excitation light intensity of 1 to 1000 mJ/cm$^2$.

The present invention relates to the method of producing the medicinal nanoparticle suspension, wherein the medicinal ingredient is a constituent of one of an anticancer drug, a vitamin, an analgesic, and an anti-inflammatory drug.

According the present invention, the poorly water-soluble or water-insoluble medicinal ingredient is added in the poor solvent to form the suspending solution. Then, the laser is irradiated to the suspending solution, so that the medicinal ingredient in the suspending solution is ground into the nanoparticles. Accordingly, it is possible to obtain the medicinal nanoparticle suspension without impurity contamination with high safety relative to a human body.

According to the present invention, the ultrasonic waves are applied to the poor solvent with the medicinal ingredient mixed therein before the laser irradiation. Accordingly, it is possible to irradiate the laser on the medicinal ingredient formed in the microparticles in advance with the ultrasonic waves, thereby efficiently and securely obtaining the medicinal nanoparticle suspension.

According to the present invention, the poor solvent with the medicinal ingredient added therein is irradiated with the laser as being continuously stirred. Accordingly, it is possible to irradiate the laser in a state that the medicinal ingredient is uniformly dispersed in the poor solvent, thereby efficiently obtaining the medicinal nanoparticle suspension with high dispersion stability.

According to the present invention, the suspending solution is placed quietly or centrifuged after the laser irradiation. The process makes it easy to separate and recover the medicinal nanoparticle suspension as a supernatant solution.

According to the present invention, the pulse laser is used as the laser. Accordingly, it is possible to increase a peak output compared to a continuous-wave laser. Therefore, the pulse laser allows the medicinal ingredient particles to be crushed certainly.

According to the present invention, the pulse laser has the pulse width of several-ten femtoseconds to several-hundred nanoseconds. Accordingly, it is possible to crush the medicinal ingredient particles efficiently and certainly.

According to the present invention, the pulse laser is irradiated at the excitation light intensity of 1 to 1000 $mJ/cm^2$. Accordingly, it is possible to crush the medicinal ingredient particles certainly, and to prevent the medicinal ingredient from being damaged.

According to the present invention, the medicinal ingredient is the constituent of one of an anticancer drug, a vitamin, an analgesic, and an anti-inflammatory drug. Thus, it is possible to obtain the medicinal nanoparticle suspension with a high applicability as the medicinal ingredient of the anticancer drug, vitamin, analgesic, or anti-inflammatory drug.

DETAILED DESCRIPTION OF THE PREFERRED EMBODIMENTS

Hereunder, embodiments of a method of producing a medicinal nanoparticle suspension according to the present invention will be described with reference to the accompanying drawings.

In the method of producing the medicinal nanoparticle suspension according to the present invention, a poorly water-soluble or water-insoluble medicinal ingredient of a drug is added in a poor solvent to form a suspending solution. Then, the suspending solution is irradiated with a laser, so that the medicinal ingredient in the suspending solution is ground to form nanoparticles of the medicinal ingredient.

The term "water-insoluble medicinal ingredient" herein refers to a medicinal ingredient with solubility in water at a room temperature of $10^{-5}$% or less (weight ratio). The term "poorly water-soluble medicinal ingredient" herein refers to a medicinal ingredient with solubility in water at a room temperature of $10^{-3}$% or less (weight ratio).

Before explaining the method of producing the medicinal nanoparticle suspension according to the present invention, a brief description will be given for a producing apparatus used in the method of the present invention.

Figure 1:
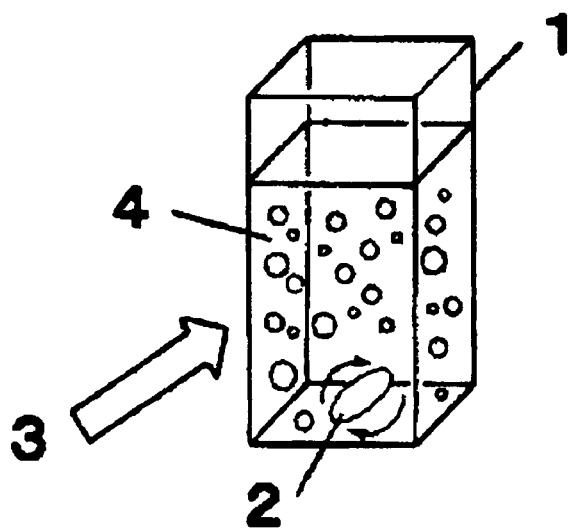
FIG. 1 is a schematic diagram illustrating one example of a producing apparatus used in a method of producing a medicinal nanoparticle suspension according to the present invention.

FIG. 1 is a schematic diagram illustrating one example of the producing apparatus used in the method of producing the medicinal nanoparticle suspension according to the present invention.

The producing apparatus includes a container (1) for retaining a poor solvent with the medical ingredient added therein, a stirring apparatus (2) for stirring the poor solvent with the medical ingredient added therein to produce a medicinal ingredient suspending solution (4), an ultrasonic generator (not shown) for applying ultrasonic waves to the medicinal ingredient suspending solution (4), and a laser irradiation device (not shown) for irradiating a laser (3) to the medicinal ingredient contained in the poor solvent in the container (1).

The container (1) is made of a material which laser light can pass through. For example, the container (1) is made of a transparent material such as glass and quartz.

In the present invention, the poor solvent to be mixed with the medicinal ingredient in the container (1) may include water, methanol, ethanol, and buffer (such as normal saline solution). The most typical poor solvent may be water. In the following explanation, water is used as the poor solvent, and the other types of poor solvents (stable against light, and to which the medicinal ingredient exhibits poor solubility or insolubility) described above may be also used instead of water.

The stirring apparatus (2) is configured to stir a mixture of water (or the other types of poor solvents) and the medicinal ingredient in the container (1). A magnetic stirrer is used as an example of the stirring apparatus (2) shown in FIG. 1, and other mechanical means such as stirring vanes may also be used.

A type of laser irradiation device to be used may include a solid state laser such as an YAG laser, a titanium-sapphire laser, and a ruby laser; a semiconductor laser such as a GaAs laser; a gas laser such as an excimer laser, an Ar ion laser, and a $CO_2$ laser; and a liquid laser such as a dye laser.

A type of oscillation to be used may include pulse oscillation.

The method of producing the medicinal nanoparticle suspension according to the present invention will be explained in detail below.

First, the poorly water-soluble or water-insoluble medicinal ingredient is mixed with water in the container (1). It is not required to add a dispersing agent, thereby preventing contamination of the dispersing agent in water. The medicinal ingredient of the drug used in the invention includes a poorly water-soluble or water-insoluble constituent of a drug among ingredients of drugs defined in Article 2 paragraph 1 of the Japanese Pharmaceutical Affairs Law. The medicinal ingredient of the drug includes medicinal ingredients of prescription drugs and nonprescription drugs.

A type of medicinal ingredient may include, but not limited to, medicinal ingredients composing anticancer drugs, vitamins, analgesics, and anti-inflammatory drugs.

Examples of the medicinal ingredients composing the anticancer drugs include ellipticine and camptothecine.

In addition to the above, the drugs include antiallergics, antiarrhythmics, antibiotics, anticoagulants, anticonvulsants/antiepileptics, muscaline antagonists, anti-mycobacterial agents, antitumor agents, immunosuppressors, antithyroid drugs, antiviral agents, anxiolytic sedatives, astringents, beta-adrenaline receptor blockers, contrast media, corticosteroid, diagnostic contrast media, diuretics, dopamine agonists, lipid regulators, muscle relaxants, parasympathomimetic agents, parathyroid calcitonine, prostaglandins, xanthine, radioactive preparations, sex hormones, soporifics, stimulants, sympathomimetic agents, thyroid preparations, vasodilators, hemostatics, immunomodulating drugs, cough medicine, diagnostic agents, and anthelmintics. The invention is applicable to medicinal ingredients composing these drugs.

The medicinal ingredients to be mixed with water may be synthesized crude powder, but it is preferable to use pretreated ground particles (micro crystals). In this case, a mean particle size of the micro crystals is preferably about 1-100 µm. This is because it takes a longer time to grind the particles larger than 100 µm so as to form the nanoparticle. Therefore, it reduces the processing efficiency. Moreover, it is impractical to grind the particles in a pretreatment process until a size thereof becomes less than 1 µm.

From the viewpoint of the efficiency of nanoparticle preparation by the laser irradiation, it is preferable to determine an appropriate amount of the medicinal ingredient to be mixed with water. The appropriate amount varies depending on the type of medicinal ingredient. For example, the amount of the medicinal ingredient may be 10-1000 µg per 1 ml of water.

In the next step, the medicinal ingredient in water is minified to a size of several hundred nm by ultrasonic application to the water mixture of the medicinal ingredient. The water mixture is then stirred using the stirring apparatus (2), such as a magnetic stirrer, to prepare the suspending solution. Then, the medicinal ingredient in the suspending solution is irradiated with the laser using the laser irradiation device, as the suspending solution is continuously stirred.

When the medicinal ingredient in water is irradiated with the laser, medicinal ingredient powder absorbs laser light, and a rapid and localized increase in a temperature occurs in a light-absorbing region of the medicinal ingredient powder.

In the light-absorbing region, the temperature increase occurs instantly upon the laser irradiation. In the meanwhile, around the light-absorbing region, the temperature increase occurs due to heat conduction. Therefore, when the medicinal ingredient powder has a relatively large particle size, a marked inner stress is created in the light-absorbing region and its periphery so that the particles are cracked, and then crushed.

When the medicinal ingredient particles exhibit high absorption relative to a wavelength of the laser light, optical absorption mainly occurs on a particle surface, thereby causing a temperature difference between a light-irradiated surface and an inner region. In such a case, the surrounding water cools the particle surface. This results in a temperature gradient between the surface and the inner region, which causes a stress in the particles and crushes them.

Accordingly, the poor solvent (e.g., water) with the medicinal ingredient mixed therein flows into the cracks of the powder caused by the laser irradiation, which facilitates crushing the particles. In addition, the poor solvent cools the medicinal ingredient powder, and makes it easy to recover the produced microparticles.

The laser to be irradiated may include, but not limited to, a laser with a wavelength of ultraviolet light, visible light, near-infrared light, and far-infrared light. A type of laser may be selected from a known solid-state laser, a semiconductor laser, a gas laser, and a liquid laser described above.

The laser with an approximate 200-800 nm wavelength is preferred. When a wavelength is shorter than 200 nm, photoenergy of the laser is easily absorbed by water. Especially, it is not negligible that the wavelength of the laser shorter than 200 nm may be absorbed by a glass- and quartz-made container. A wavelength longer than 800 nm is likely to result in inefficient crush of the particles, because the medicinal ingredient generally does not absorb light in this wavelength range.

An example of the laser used in the invention includes the 2nd harmonic (wavelength of 532 nm) of a Nd3+:YAG laser (basic wavelength of 1064 nm), the 3rd harmonic (wavelength of 355 nm) thereof, the 4th harmonic (wavelength of 266 nm) thereof, an excimer laser (wavelengths of 193 nm, 248 nm, 308 nm, and 351 nm), a nitrogen laser (wavelength of 337 nm), and an Ar ion laser (wavelength of 488 nm or 514 nm).

A type of oscillation of the laser to be irradiated may preferably include pulse oscillation. It is preferable to use the pulse laser with a pulse width of several-ten femtoseconds to several-hundred nanoseconds, in view of efficiency of crushing the medicinal ingredient.

An excitation light intensity of the laser depends on the type of medicinal ingredient. For example, a preferable range of the excitation light intensity is 1-1000 $mJ/cm^2$. The excitation light intensity lower than 1 $mJ/cm^2$ may not be high enough to crush the medicinal ingredient. The excitation light intensity higher than 1000 $mJ/cm^2$ may degrade the medicinal ingredient.

An appropriate range of a pulse repeat frequency may be 0.1-1000 Hz. In terms of the process efficiency, a high repeat frequency is preferred. However, a high repeat frequency heats water temperature to make a temperature difference between water and the medicinal ingredient particles small, thereby lowering the crushing efficiency.

Thus, it is preferred to set a high repeat frequency to the extent that the water temperature does not excessively increase. When the YAG laser is used, the repeat frequency is set within a range of 1-100 Hz.

In the invention, a cooling device may be used to cool the container (1) for controlling the temperature of the medicinal ingredient suspending solution in the container (1) to be lower than a predetermined temperature (for example, 10° C. or lower). Thus, it is possible to avoid a reduction in process efficiency resulting from an increase in the water temperature caused by the laser irradiation as described above.

As described above, when the water temperature is maintained lower than a certain temperature, it is possible to generate the marked temperature difference between water and the medicinal ingredient particle surface as well as between the medicinal ingredient particle surface and the inner region thereof. The medicinal ingredient particles are then easily crushed upon the laser irradiation.

After the laser irradiation, the medicinal ingredient suspending solution (4) is placed quietly or centrifuged for a certain period of time.

The process makes it easier to recover the medicinal nanoparticle suspension as the supernatant solution from the suspending solution (4) containing the nanoparticles of the medicinal ingredient formed through the laser irradiation.

The following example is shown to clarify an effect of the present invention, and the present invention is not limited thereto.

The medicinal nanoparticle suspension was produced using the producing apparatus shown in FIG. 1.

Ellipticine microcrystals (4 mg) as a raw material were added to water (1000 ml) contained in the container (1). The ultrasonic waves were then applied to water in the container for 15 minutes, so that ellipticine was formed in several hundred-nm microparticles.

In this state (before the laser irradiation), most of the ellipticine microparticles were precipitated on the container bottom within a short time, which made the supernatant solution almost transparent.

In the next step, water in the container was stirred using a magnetic stirrer. The ellipticine microparticles dispersing in water were then irradiated with the 3rd harmonic (wavelength: 355 nm, half pulse width: 7 ns, repeat frequency: 10 Hz) of a nanosecond Nd3+: YAG laser at an excitation light intensity of 100 mJ/cm$^2$ for 10 seconds using the laser irradiation device so as to induce ablation. The ellipticine microparticles were ground in water, so that yellow and transparent colloid solution was obtained.

Figure 2:
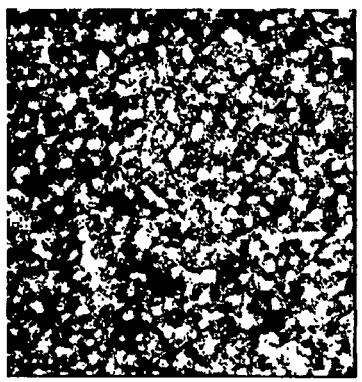
FIG. 2 is a scanning electron microscopy (SEM) picture of the medicinal nanoparticle suspension obtained by the method according to the present invention.
Figure 3:
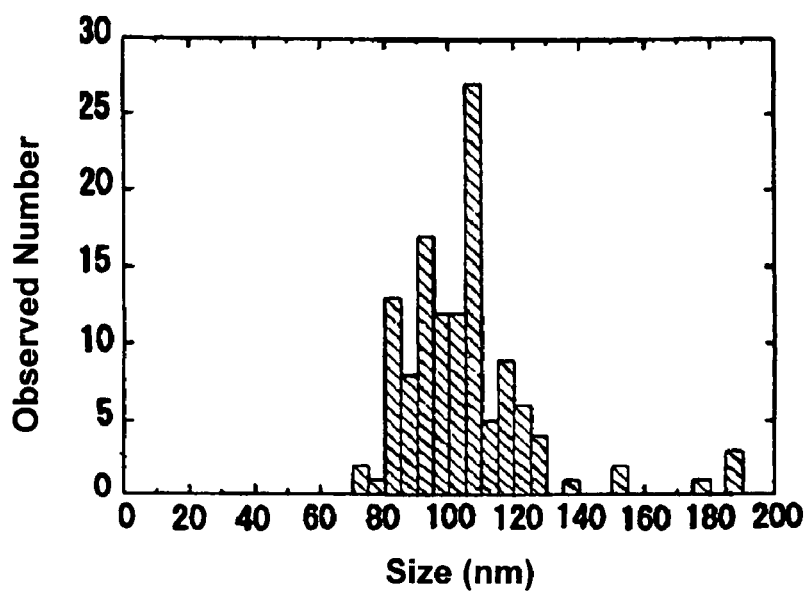
FIG. 3 is a histogram showing a measurement result of a particle size of the medicinal nanoparticle suspension obtained by the method according to the present invention.

The obtained colloid solution was placed quietly for 1 day. The supernatant solution was collected and dripped on a hydrophobic-treated silicon board. After a drying process, the ellipticine particles were observed by scanning electron microscopy (SEM), and a size of the ellipticine nanoparticles was measured. A SEM photograph is shown in FIG. 2, and a histogram of the size of the ellipticine nanoparticles is shown in FIG. 3.

As a result of the SEM observation and measurement, it was confirmed that the ellipticine nanoparticles with a mean particle size about 100 nm were obtained.

The medicinal nanoparticle suspension thus obtained according to the present invention is very safe without impurity contamination, and is appropriate for administration to a human body. Therefore, it is expected to use the medicinal nanoparticle suspension in a drug delivery system.

A Japanese patent application No. 2006-135878, filed on May 15, 2006, is hereby incorporated by reference in the application.

What is claimed is:

1. A method of producing a medicinal nanoparticle suspension, comprising the steps of:
    adding a poorly water-soluble or water-insoluble medicinal ingredient of a drug into a poor solvent to form a suspending solution; and
    irradiating the suspending solution with a laser having a wavelength that is absorbed by the medicinal ingredient to grind the medicinal ingredient in the suspending solution to form nanoparticles.

2. The method according to claim 1, further comprising the step of applying ultrasonic waves to the poor solvent with the medicinal ingredient mixed therein, before the step of irradiating the suspending solution with the laser.

3. The method according to claim 1, wherein, in the step of irradiating the suspending solution with the laser, said poor solvent with the medicinal ingredients mixed therein is stirred.

4. The method according to claim 1, further comprising the step of placing the suspending solution quietly or centrifuging the suspending solution, after the step of irradiating the suspending solution with the laser.

5. The method according to claim 1, wherein, in the step of irradiating the suspending solution with the laser, a pulse laser is used.

6. The method according to claim 5, wherein, in the step of irradiating the suspending solution with the laser, said pulse laser has a pulse width ranged from several-ten femtoseconds to several-hundred nanoseconds.

7. The method according to claim 5, wherein, in the step of irradiating the suspending solution with the laser, said pulse laser is irradiated at an excitation light intensity of 1 to 1000 mJ/cm$^2$.

8. The method according to claim 1, wherein, in the step of forming the suspending solution, said medicinal ingredient includes a constituent of one of an anticancer drug, a vitamin analgesic, and an anti-inflammatory drug.

* * * * *